US00PP09860P

United States Patent [19]

Zaiger et al.

[11] Patent Number: Plant 9,860

[45] Date of Patent: Apr. 15, 1997

[54] PEACH TREE SUPER RICH

[76] Inventors: Chris F. Zaiger, 929 Grimes Ave.; Gary N. Zaiger, 1907 Elm Ave.; Leith M. Gardner, 1207 Grimes Ave.; Grant G. Zaiger, 4005 California Ave., all of Modesto, Calif. 95358

[21] Appl. No.: 593,003

[22] Filed: Jan. 29, 1996

[51] Int. Cl.[6] ..... A01H 5/00

[52] U.S. Cl. ..... Plt./43.1

[58] Field of Search ..... Plt./43.1

*Primary Examiner*—James R. Feyrer

[57] ABSTRACT

A new and distinct variety of peach, *Prienus persica,* its novelty consisting of the following unique combination of features that are desirable in a new variety:

1. Heavy and regular production of large size fruit.
2. Fruit ripening in the early maturity season.
3. Fruit with good flavor and eating quality.
4. Fruit with firm flesh, good handling and shipping quality.
5. Relatively uniform maturity of fruit throughout the tree.
6. An attractive fruit with a high degree of red skin color.

1 Drawing Sheet

ORIGIN OF THE VARIETY

The present new variety of peach tree was originated by us in our experimental orchard located near Modesto, Calif. as a first generation cross between Earlirich Peach (U.S. Plant Pat. No. 9,002) and a selected seedling with field identification number 104LB628. The pollen parent (104LB628), originated from a third generation cross between an open pollinated seedling of May Grand Nectarine (U.S. Plant Pat. No. 2,794) crossed with May Crest Peach (U.S. Plant Pat. No. 4,064). A large group of these first generation seedlings were planted and maintained under careful observation by us, during which time we recognized its distinct and desirable fruit characteristics described above and selected the seedling for asexual reproduction and commercialization.

ASEXUAL REPRODUCTION OF THE VARIETY

Asexual reproduction of the present new variety by budding was performed by us in our experimental orchard located near Modesto, Calif. and shows that all characteristics run true to the originial tree and are established and transmitted through succeeding propagations.

SUMMARY OF THE VARIETY

Our new and distinct variety of peach tree is of large size, vigorous, upright growth, a productive and regular bearer of large, yellow flesh clingstone fruit, with good flavor and eating quality. The fruit is further characterized by having firm flesh with good handling and shipping quality, relatively uniform ripening of early maturing fruit with an attractive high red skin color and, in comparison to one of its pollen parent May Crest Peach (U.S. Plant Pat. No. 4,064), the fruit of the new variety matures approximately 9 days earlier, has greater production of larger size fruit, with a higher degree of attractive red skin color.

BRIEF DESCRIPTION OF THE PHOTOGRAPH

The accompanying photograph shows a color illustration of typical specimens of the fruit and foliage of the present new variety of peach tree. The illustration is of the upper and lower surface of the leaves, with the exterior and a sectional view of a fruit divided in the suture plane to show flesh coloration, pit cavity and a stone remaining in place. The photograph was taken shortly after being picked (shipping ripe), and the colors are as nearly true as is reasonably possible in a color representation of this type.

DESCRIPTION OF THE VARIETY

The following is a detailed botanical description of our new peach tree, its flowers, fruit and foliage as based on observation of specimens grown in our experimental orchard located near Modesto, Calif. with color terminology (except those in common terms) in accordance with Reinhold Color Atlas by A. Kornerup and J. H. Wanscher.

Tree:
- *Size.*—Large.
- *Vigor.*—Vigorous.
- *Growth.*—Upright.
- *Density.*—Medium dense.
- *Bearing.*—Regular.
- *Productivity.*—Productive.

Trunk:
- *Size.*—Medium.
- *Texture.*—Medium shaggy.
- *Color.*—Leather brown to dark brown (6-E-6) to (6-F-6).

Branches:
- *Size.*—Medium.
- *Texture.*—Smooth to medium rough.
- *Lenticels.*—Numerous. Large size.
- *Color.*—Light brown to brown, varies with maturity.

Leaves:
- *Size.*—Large Average length 6'. Average width 1 ½ '.
- *Form.*—Lanceolate, pointed.
- *Texture.*—Smooth.
- *Margin.*—Crenate.
- *Thickness.*—Medium.
- *Petiole.*—Medium length. Medium thickness.
- *Glands.*—Number varies from 1 to 4. Average number 2. Reniform. Medium size. Located on base of leaf blade and upper portion of the petiole.
- *Color.*—Upper surace — green to dark green (29F-7) to (29-F-8). Lower surface — grayish green to green (29-E-7) to (29-E-8).

Flower Buds:
- *Size.*—Large.
- *Form.*—Plump.
- *Pubescence.*—Pubescent.

Flowers:
- *Size.*—Large, showy.
- *Blooming period.*—Mar. 1, 1994 to Mar. 6, 1994.
- *Pollen.*—Present, self fertile.
- *Color.*—Pink.

Fruit:

*Maturity when described.*—Shipping ripe.

*Date of first picking.*—May 12, 1994.

*Date of last picking.*—May 16, 1994.

*Size.13* Large. Average diameter axially 2¾". Average transversely in suture plane 2¾".

*Form.*—Nearly globose, slightly flattened at stem end, slight apical point.

*Suture.*—Shallow, nearly smooth, extends from base to apex.

*Ventral surface.*—Nearly rounded.

*Base.*—Retuse.

*Cavity.*—Rounded, slightly elongated in suture plane. Average depth ½'. Average breadth 15/16'.

*Apex.*—Varies from round to slight point.

*Skin:*

*Thickness.*—Medium.

*Texture.*—Medium, tenacious to flesh.

*Tendency to crack.*—None.

*Down.*—Moderate amount. Medium length.

*Color.*—Yellow to golden yellow ground color (4-A-6) to (5-A-6). Overspread with red to lake red (9-C-7) to (9-C-8).

Flesh:

*Ripens.*—Relatively even, slightly earlier near apex.

*Texture.*—Firm.

*Fibers.*—Few, small, tender.

*Juice.*—Moderate.

*Aroma.*—Moderate.

*Amygdalin.*—Undetected.

*Flavor.*—Good.

*Eating quality.*—Good.

*Color.*—Yellow to golden yellow (5-A-6) to (5-A-7). Pit cavity, yellowish gray to grayish yellow (4-B-3) to (4-B-4).

Stone:

*Type.*—Clingstone.

*Size.*—Medium to large. Average length ¼". Average width 1". Average thickness ⅝".

*Form.*—Varies from ovate to obovate.

*Base.*—Mostly straight, varies from straight to round.

*Apex.*—Varies from round to cuspidate.

*Surface.*—Irregularly furrowed toward apex, pitted toward base.

*Ridges.*—Rounded. Sides, mostly equal, varies from equal to unequal.

*Tendency to split.*—Slight.

*Color.*—Light tan to light brown (5-C-4) to (6-D-4).

Use: Dessert.

*Market.*—local and long distance.

Keeping quality: Good.

Shipping quality: Good.

The present new variety of peach tree, its flowers, foliage and fruit herein described may vary in slight detail due to climate, soil conditions and cultural practices under which the variety is grown; the present description is that of the variety grown under the ecological conditions prevailing near Modesto, Calif.

We claim:

1. A new and distinct variety of peach tree, substantially as illustrated and described, characterized by its large size, vigorous, upright growth and a regular and productive bearer of large, firm, early maturing, yellow flesh, clingstone fruit with good flavor and eating quality; the fruit is further characterized by having good handling and shipping quality, having a high degree of attractive red skin color and, in comparison to the variety May Crest Peach (U.S. Plant Pat. No. 4,064), the new variety has greater production of larger size fruit, maturing approximately 9 days earlier.

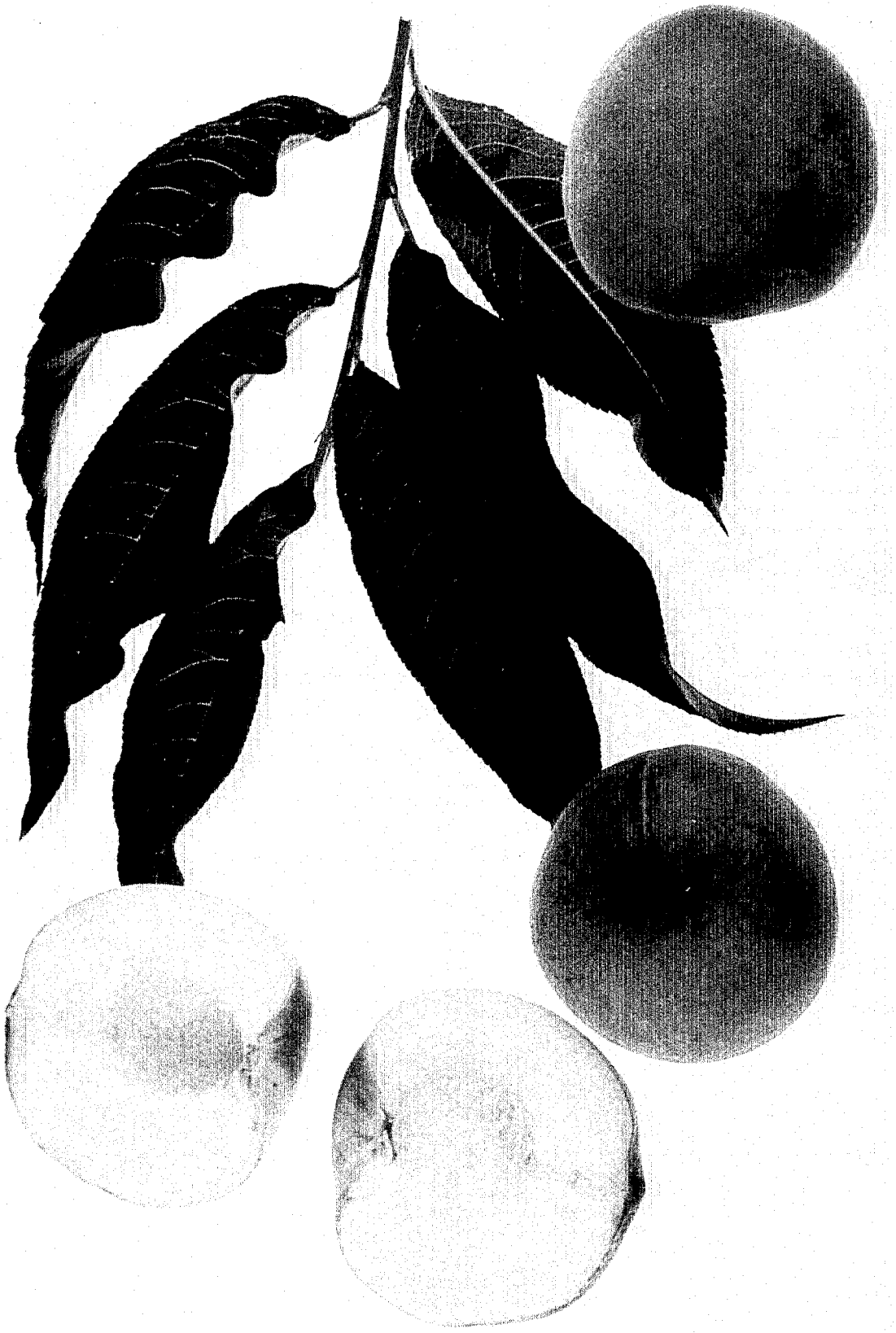

* * * * *